United States Patent
Bita

(10) Patent No.: US 8,711,361 B2
(45) Date of Patent: Apr. 29, 2014

(54) METHODS AND DEVICES FOR DETECTING AND MEASURING ENVIRONMENTAL CONDITIONS IN HIGH PERFORMANCE DEVICE PACKAGES

(75) Inventor: Ion Bita, San Jose, CA (US)

(73) Assignee: QUALCOMM, Incorporated, San Diego, CA (US)

( * ) Notice: Subject to any disclaimer, the term of this patent is extended or adjusted under 35 U.S.C. 154(b) by 348 days.

(21) Appl. No.: 12/613,396

(22) Filed: Nov. 5, 2009

(65) Prior Publication Data

US 2011/0102800 A1  May 5, 2011

(51) Int. Cl.
*G01J 3/45* (2006.01)

(52) U.S. Cl.
USPC .......................... 356/454; 356/519

(58) Field of Classification Search
USPC ......................... 356/450, 454, 519
See application file for complete search history.

(56) References Cited

U.S. PATENT DOCUMENTS

| | | |
|---|---|---|
| 4,441,791 A | 4/1984 | Hornbeck |
| 4,571,603 A | 2/1986 | Hornbeck et al. |
| 4,748,366 A | 5/1988 | Taylor |
| 4,850,709 A | 7/1989 | Ban et al. |
| 4,859,060 A | 8/1989 | Katagiri et al. |
| 4,954,789 A | 9/1990 | Sampsell |
| 5,083,857 A | 1/1992 | Hornbeck |
| 5,216,537 A | 6/1993 | Hornbeck |
| 5,226,099 A | 7/1993 | Mignardi et al. |
| 5,489,952 A | 2/1996 | Gove et al. |
| 5,526,172 A | 6/1996 | Kanack |
| 5,530,240 A | 6/1996 | Larson et al. |
| 5,550,373 A | 8/1996 | Cole et al. |
| 5,551,293 A | 9/1996 | Boysel et al. |
| 5,561,523 A | 10/1996 | Blomberg et al. |
| 5,629,521 A | 5/1997 | Lee et al. |
| 5,771,321 A | 6/1998 | Stern |
| 5,815,141 A | 9/1998 | Phares |
| 5,894,686 A | 4/1999 | Parker et al. |
| 5,973,817 A | 10/1999 | Robinson et al. |
| 5,977,945 A | 11/1999 | Ohshima |
| 6,014,121 A | 1/2000 | Aratani et al. |
| 6,040,937 A | 3/2000 | Miles |
| 6,295,048 B1 | 9/2001 | Ward et al. |
| 6,304,297 B1 | 10/2001 | Swan |
| 6,307,194 B1 | 10/2001 | Fitzgibbons et al. |

(Continued)

FOREIGN PATENT DOCUMENTS

| | | |
|---|---|---|
| DE | 3832185 | 3/1990 |
| EP | 0 649 010 | 4/1995 |

(Continued)

OTHER PUBLICATIONS

ISR and WO dated Feb. 4, 2011 in PCT/US10/055015.

(Continued)

*Primary Examiner* — Tarifur Chowdhury
*Assistant Examiner* — Jonathan Hansen
(74) *Attorney, Agent, or Firm* — Knobbe Martens Olson & Bear, LLP

(57) ABSTRACT

An environmental condition sensing device includes an interferometric modulator with optical properties, which change in response to being exposed to a predetermined environmental threshold or condition. The device includes an environmental reactive layer, which alters composition, in an optically-detectable manner, in response to being exposed to a predetermined environmental threshold or condition.

19 Claims, 14 Drawing Sheets

(56) References Cited

U.S. PATENT DOCUMENTS

| | | |
|---|---|---|
| 6,323,834 B1 | 11/2001 | Colgan et al. |
| 6,407,862 B2 | 6/2002 | Moshrefzadeh |
| 6,412,962 B1 | 7/2002 | Kaspar |
| 6,549,107 B2 | 4/2003 | Lim et al. |
| 6,617,963 B1 | 9/2003 | Watters et al. |
| 6,650,455 B2 | 11/2003 | Miles |
| 6,666,561 B1 | 12/2003 | Blakley |
| 6,674,562 B1 | 1/2004 | Miles et al. |
| 6,680,792 B2 | 1/2004 | Miles |
| 6,737,979 B1 | 5/2004 | Smith et al. |
| 6,776,538 B2 | 8/2004 | Whitney et al. |
| 6,819,469 B1 | 11/2004 | Koba |
| 6,829,132 B2 | 12/2004 | Martin et al. |
| 7,042,643 B2 | 5/2006 | Miles |
| 7,046,374 B1 | 5/2006 | Barbarossa |
| 7,123,216 B1 | 10/2006 | Miles |
| 7,138,984 B1 | 11/2006 | Miles |
| 7,280,265 B2 | 10/2007 | Miles |
| 7,321,417 B2 | 1/2008 | Bleeker |
| 7,327,510 B2 | 2/2008 | Cummings et al. |
| 7,330,369 B2 | 2/2008 | Tran |
| 7,369,294 B2 | 5/2008 | Gally et al. |
| 7,388,706 B2 | 6/2008 | Miles |
| 7,425,453 B1* | 9/2008 | Hutchens et al. ............. 436/165 |
| 7,460,246 B2 | 12/2008 | Kothari |
| 7,535,466 B2 | 5/2009 | Sampsell et al. |
| 7,551,287 B2 | 6/2009 | Zribi et al. |
| 7,586,484 B2 | 9/2009 | Sampsell et al. |
| 7,595,926 B2 | 9/2009 | Sasagawa et al. |
| 7,623,752 B2 | 11/2009 | Gally et al. |
| 7,653,371 B2 | 1/2010 | Floyd |
| 7,657,242 B2 | 2/2010 | Floyd |
| 7,660,028 B2 | 2/2010 | Lan |
| 7,787,130 B2 | 8/2010 | Webster |
| 7,787,171 B2 | 8/2010 | Webster |
| 7,808,703 B2 | 10/2010 | Gally et al. |
| 7,852,483 B2 | 12/2010 | Kothari |
| 7,852,491 B2 | 12/2010 | Webster |
| 7,860,668 B2 | 12/2010 | Khazeni |
| 7,881,686 B2 | 2/2011 | Floyd |
| 7,916,103 B2 | 3/2011 | Palmateer |
| 8,077,326 B1 | 12/2011 | Webster |
| 2002/0075555 A1* | 6/2002 | Miles ........................... 359/291 |
| 2003/0072070 A1 | 4/2003 | Miles |
| 2003/0112507 A1 | 6/2003 | Divelbiss et al. |
| 2003/0117382 A1 | 6/2003 | Pawlowski et al. |
| 2003/0128197 A1 | 7/2003 | Turner et al. |
| 2004/0024580 A1 | 2/2004 | Salmonsen et al. |
| 2005/0001797 A1 | 1/2005 | Miller et al. |
| 2005/0046919 A1 | 3/2005 | Taguchi et al. |
| 2005/0068254 A1 | 3/2005 | Booth |
| 2006/0018348 A1 | 1/2006 | Przybyla et al. |
| 2006/0066557 A1 | 3/2006 | Floyd |
| 2006/0066595 A1 | 3/2006 | Sampsell et al. |
| 2006/0066596 A1 | 3/2006 | Sampsell et al. |
| 2006/0076632 A1 | 4/2006 | Palmateer et al. |
| 2006/0077521 A1 | 4/2006 | Gally et al. |
| 2006/0176241 A1 | 8/2006 | Sampsell |
| 2006/0202933 A1 | 9/2006 | Pasch et al. |
| 2006/0250337 A1 | 11/2006 | Miles |
| 2007/0023851 A1 | 2/2007 | Hartzell et al. |
| 2007/0115480 A1* | 5/2007 | Zhang et al. ................. 356/503 |
| 2007/0138391 A1 | 6/2007 | Garber et al. |
| 2007/0200839 A1 | 8/2007 | Sampsell |
| 2007/0201787 A1* | 8/2007 | Cross et al. ..................... 385/12 |
| 2007/0242008 A1 | 10/2007 | Cummings |
| 2007/0247406 A1 | 10/2007 | Zhou et al. |
| 2008/0008625 A1* | 1/2008 | Thomas et al. ............ 422/82.05 |
| 2008/0112031 A1 | 5/2008 | Gally et al. |
| 2008/0196814 A1 | 8/2008 | Yang |
| 2009/0207473 A1 | 8/2009 | Bita et al. |
| 2009/0244679 A1 | 10/2009 | Khazeni et al. |
| 2009/0267869 A1 | 10/2009 | Gally et al. |
| 2009/0267953 A1 | 10/2009 | Sampsell et al. |
| 2009/0308452 A1 | 12/2009 | Sasagawa et al. |
| 2010/0117761 A1 | 5/2010 | Floyd |
| 2010/0123706 A1 | 5/2010 | Lan |
| 2010/0220248 A1 | 9/2010 | Miles |
| 2011/0071775 A1 | 3/2011 | Khazeni |
| 2011/0085278 A1 | 4/2011 | Floyd |
| 2011/0115690 A1 | 5/2011 | Cummings |
| 2011/0148828 A1 | 6/2011 | Sampsell et al. |

FOREIGN PATENT DOCUMENTS

| | | |
|---|---|---|
| EP | 0 725 380 | 8/1996 |
| EP | 1126278 A2 | 8/2001 |
| JP | 2002287047 A | 10/2002 |
| WO | WO-03056367 A1 | 7/2003 |
| WO | WO 2004/066256 | 8/2004 |
| WO | WO-2004068460 A1 | 8/2004 |
| WO | WO 2005/066596 | 7/2005 |

OTHER PUBLICATIONS

Brank et al., Sep. 2001, RF MEMS-based tunable filters, International Journal of RF and Microwave Computer-Aided Engineering, 11(5):276-284.

Miles, A New Reflective FPD Technology Using Interferometric Modulation, Journal of the SID 5/4, 1997, pp. 379-382.

Miles, "MEMS-based interferometric modulator for display applications," Proceedings of SPIE, vol. 3876, Aug. 1999, pp. 20-281.

Miles et al., 10.1: Digital Paper™ for reflective displays, SID 02 Digest, pp. 115-117, 2002.

Winton, John M., A novel way to capture solar energy, Chemical Week, pp. 17-18 (May 15, 1985).

Wu, Design of a Reflective Color LCD Using Optical Interference Reflectors, ASIA Display '95, pp. 929-931 (Oct. 16, 1995).

IPRP dated May 18, 2012 in PCT/US10/055015.

* cited by examiner

| | Column Output Signals | |
|---|---|---|
| | $+V_{bias}$ | $-V_{bias}$ |
| Row Output Signals  0 | Stable | Stable |
| $+\Delta V$ | Relax | Actuate |
| $-\Delta V$ | Actuate | Relax |

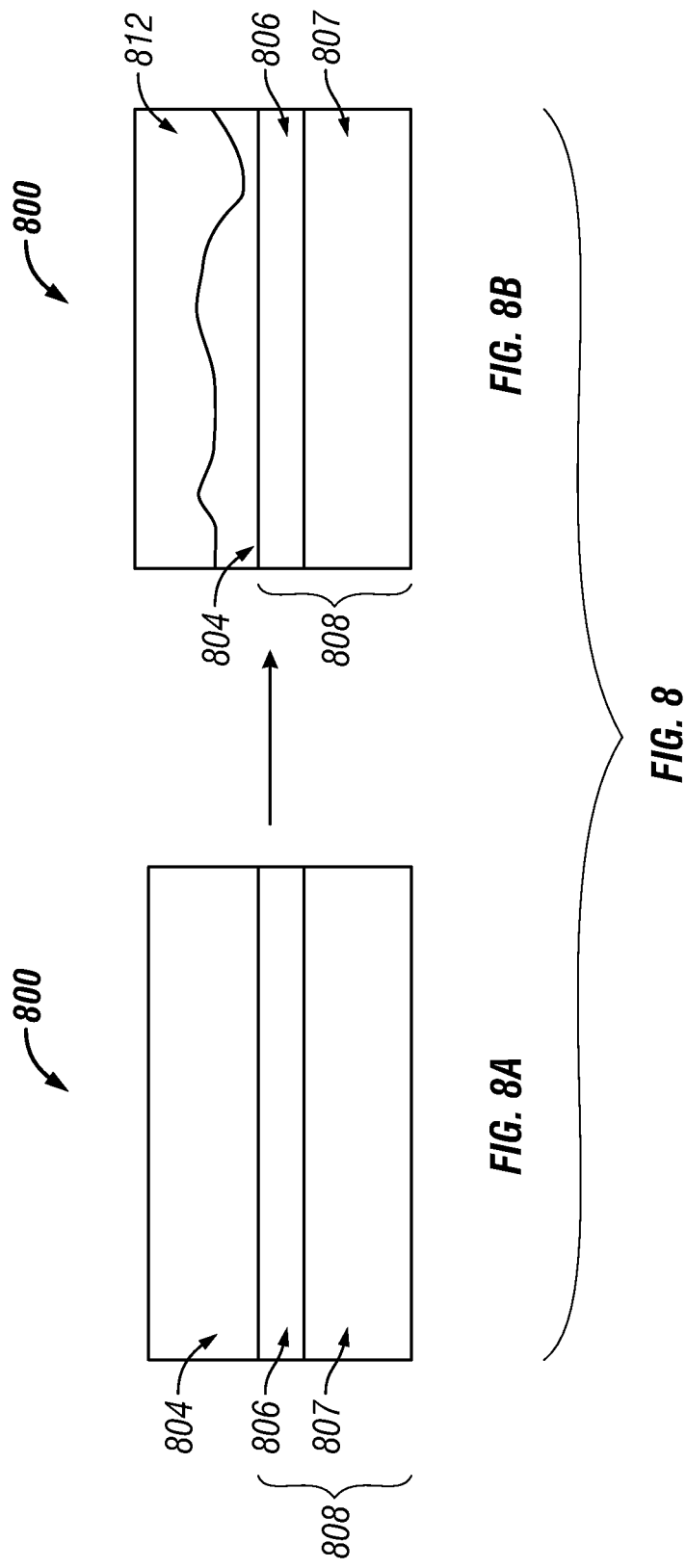

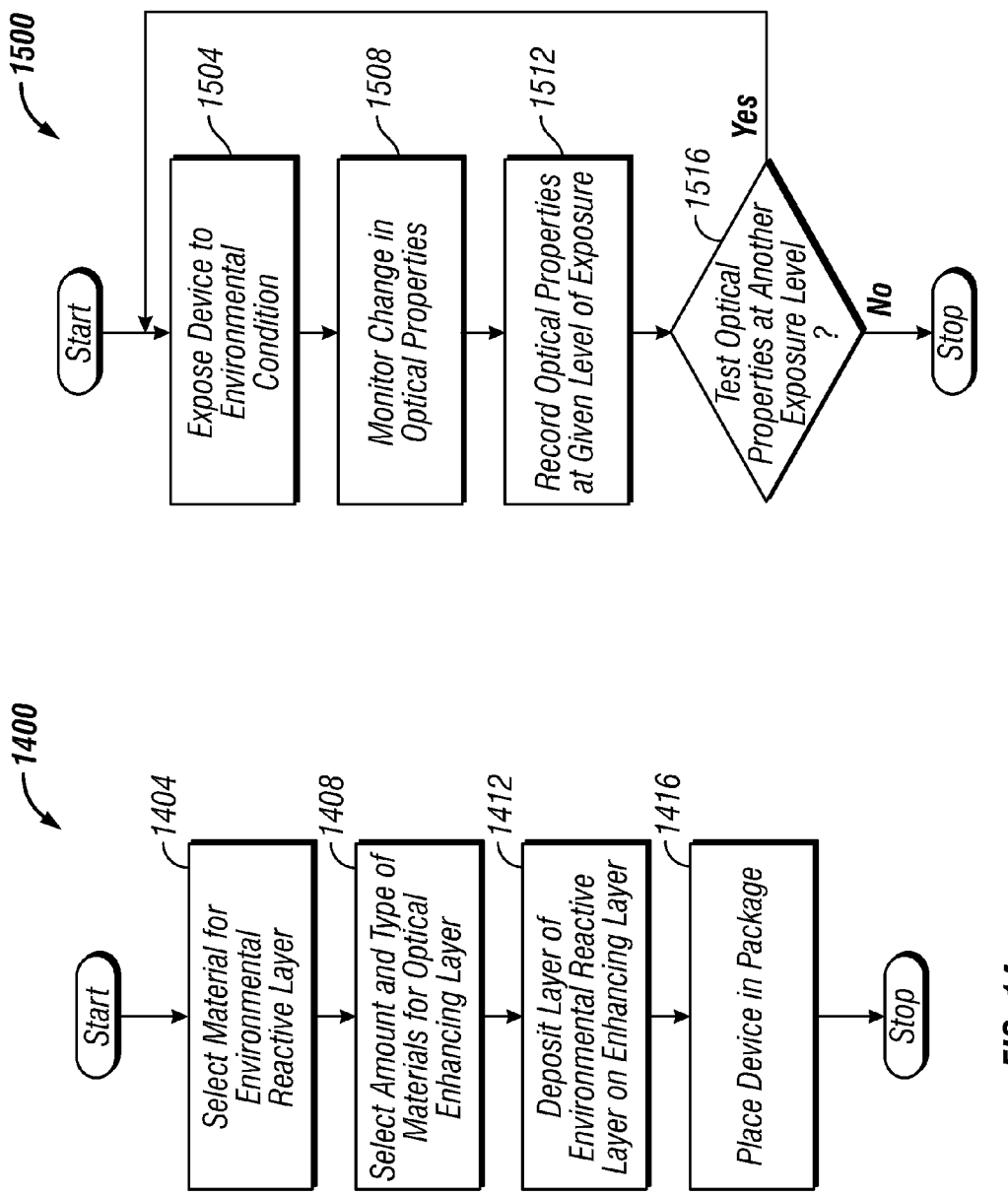

METHODS AND DEVICES FOR DETECTING AND MEASURING ENVIRONMENTAL CONDITIONS IN HIGH PERFORMANCE DEVICE PACKAGES

BACKGROUND

1. Field of the Invention

The present invention relates to devices sensitive to environmental exposure including organic light emitting diode devices (OLED) and microelectromechanical systems (MEMS).

2. Description of Related Technology

Microelectromechanical systems (MEMS) include micro mechanical elements, actuators, and electronics. Micromechanical elements may be created using deposition, etching, and or other micromachining processes that etch away parts of substrates and/or deposited material layers or that add layers to form electrical and electromechanical devices. One type of MEMS device is called an interferometric modulator. As used herein, the term interferometric modulator or interferometric light modulator refers to a device that selectively absorbs and/or reflects light using the principles of optical interference. In certain embodiments, an interferometric modulator may comprise a pair of conductive plates, one or both of which may be transparent and/or reflective in whole or part and capable of relative motion upon application of an appropriate electrical signal. In a particular embodiment, one plate may comprise a stationary layer deposited on a substrate and the other plate may comprise a metallic membrane separated from the stationary layer by an air gap. As described herein in more detail, the position of one plate in relation to another can change the optical interference of light incident on the interferometric modulator. Such devices have a wide range of applications, and it would be beneficial in the art to utilize and/or modify the characteristics of these types of devices so that their features can be exploited in improving existing products and creating new products that have not yet been developed.

BRIEF DESCRIPTION OF THE DRAWINGS

FIG. 8A is a block diagram illustrating an embodiment of an environmental condition detection device in its initial state.

FIG. 8B is a block diagram illustrating an alternative embodiment of an environmental condition detection device after partial chemical modification.

FIG. 14 is a flowchart of an embodiment of a process of manufacture of an embodiment of the environmental condition detection device.

FIG. 15 is a flowchart of an embodiment of a process of measuring response of an embodiment of the environmental condition detection device to an environmental condition.

DETAILED DESCRIPTION

The following detailed description is directed to certain specific embodiments. However, the teachings herein can be applied in a multitude of different ways. In this description, reference is made to the drawings wherein like parts are designated with like numerals throughout. The embodiments may be implemented in any device that is configured to display an image, whether in motion (e.g., video) or stationary (e.g., still image), and whether textual or pictorial. More particularly, it is contemplated that the embodiments may be implemented in or associated with a variety of electronic devices such as, but not limited to, mobile telephones, wireless devices, personal data assistants (PDAs), hand-held or portable computers, GPS receivers/navigators, cameras, MP3 players, camcorders, game consoles, wrist watches, clocks, calculators, television monitors, flat panel displays, computer monitors, auto displays (e.g., odometer display, etc.), cockpit controls and/or displays, display of camera views (e.g., display of a rear view camera in a vehicle), electronic photographs, electronic billboards or signs, projectors, architectural structures, packaging, and aesthetic structures (e.g., display of images on a piece of jewelry). MEMS devices of similar structure to those described herein can also be used in non-display applications such as in electronic switching devices.

Many devices, including MEMS devices, are extremely sensitive to environmental conditions and require special packaging (encapsulation) that is extremely impermeable. Even small changes in environmental conditions, such as the presence of a small amount of a gas species, can adversely affect the functionality of such a device. Certain materials readily react in the presence of specific gas species (e.g. water, oxygen, etc.). The reaction may then cause certain optical properties of the material to change. Depending on the materials used and the detection method, it can be inferred what amount of gas the material has been exposed to, which under specific conditions can be used to advantage. Methods and devices are described herein which are configured to alter in response to exposure to a pre-determined environmental condition or set of conditions. These devices may comprise interferometric modulators which, given their enhanced optical properties, are capable of detecting such alterations. These devices can be used in various applications, such as consumer-level packaging where conditions during shipping and/or storage must be monitored to ensure quality. These devices can also be used to monitor environmental conditions in the packaging of MEMS devices.

Figure 1:
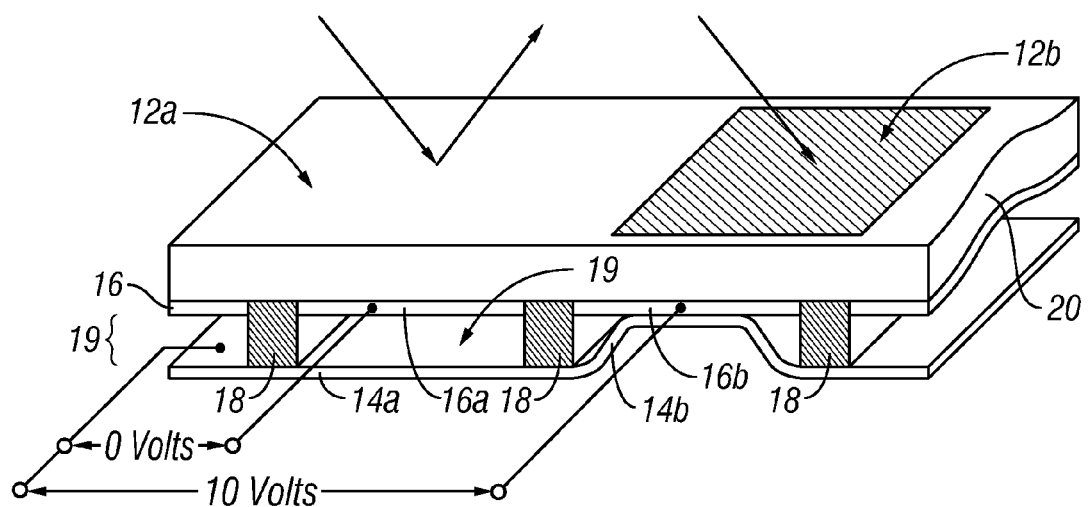
FIG. 1 is an isometric view depicting a portion of one embodiment of an interferometric modulator display in which a movable reflective layer of a first interferometric modulator is in a relaxed position and a movable reflective layer of a second interferometric modulator is in an actuated position.

One interferometric modulator display embodiment comprising an interferometric MEMS display element is illustrated in FIG. 1. In these devices, the pixels are in either a bright or dark state. In the bright ("relaxed" or "open") state, the display element reflects a large portion of incident visible light to a user. When in the dark ("actuated" or "closed") state, the display element reflects little incident visible light to the user. Depending on the embodiment, the light reflectance properties of the "on" and "off" states may be reversed. MEMS pixels can be configured to reflect predominantly at selected colors, allowing for a color display in addition to black and white.

FIG. 1 is an isometric view depicting two adjacent pixels in a series of pixels of a visual display, wherein each pixel comprises a MEMS interferometric modulator. In some embodiments, an interferometric modulator display comprises a row/column array of these interferometric modulators. Each interferometric modulator includes a pair of reflective layers positioned at a variable and controllable distance from each other to form a resonant optical gap with at least one variable dimension. In one embodiment, one of the reflective layers may be moved between two positions. In the first position, referred to herein as the relaxed position, the movable reflective layer is positioned at a relatively large distance from a fixed partially reflective layer. In the second position, referred to herein as the actuated position, the movable reflective layer is positioned more closely adjacent to the partially reflective layer. Incident light that reflects from the two layers interferes constructively or destructively depending on the position of the movable reflective layer, producing either an overall reflective or non-reflective state for each pixel.

The depicted portion of the pixel array in FIG. 1 includes two adjacent interferometric modulators 12a and 12b. In the interferometric modulator 12a on the left, a movable reflective layer 14a is illustrated in a relaxed position at a predetermined distance from an optical stack 16a, which includes a partially reflective layer. In the interferometric modulator 12b on the right, the movable reflective layer 14b is illustrated in an actuated position adjacent to the optical stack 16b.

The optical stacks 16a and 16b (collectively referred to as optical stack 16), as referenced herein, typically comprise several fused layers, which can include an electrode layer, such as indium tin oxide (ITO), a partially reflective layer, such as chromium, and a transparent dielectric. The optical stack 16 is thus electrically conductive, partially transparent and partially reflective, and may be fabricated, for example, by depositing one or more of the above layers onto a transparent substrate 20. The partially reflective layer can be formed from a variety of materials that are partially reflective such as various metals, semiconductors, and dielectrics. The partially reflective layer can be formed of one or more layers of materials, and each of the layers can be formed of a single material or a combination of materials.

In some embodiments, the layers of the optical stack 16 are patterned into parallel strips, and may form row electrodes in a display device as described further below. The movable reflective layers 14a, 14b may be formed as a series of parallel strips of a deposited metal layer or layers (orthogonal to the row electrodes of 16a, 16b) to form columns deposited on top of posts 18 and an intervening sacrificial material deposited between the posts 18. When the sacrificial material is etched away, the movable reflective layers 14a, 14b are separated from the optical stacks 16a, 16b by a defined gap 19. A highly conductive and reflective material such as aluminum may be used for the reflective layers 14, and these strips may form column electrodes in a display device. Note that FIG. 1 may not be to scale. In some embodiments, the spacing between posts 18 may be on the order of 10-100 um, while the gap 19 may be on the order of <1000 Angstroms.

With no applied voltage, the gap 19 remains between the movable reflective layer 14a and optical stack 16a, with the movable reflective layer 14a in a mechanically relaxed state, as illustrated by the pixel 12a in FIG. 1. However, when a potential (voltage) difference is applied to a selected row and column, the capacitor formed at the intersection of the row and column electrodes at the corresponding pixel becomes charged, and electrostatic forces pull the electrodes together. If the voltage is high enough, the movable reflective layer 14 is deformed and is forced against the optical stack 16. A dielectric layer (not illustrated in this Figure) within the optical stack 16 may prevent shorting and control the separation distance between layers 14 and 16, as illustrated by actuated pixel 12b on the right in FIG. 1. The behavior is the same regardless of the polarity of the applied potential difference.

FIGS. 2 through 5 illustrate one exemplary process and system for using an array of interferometric modulators in a display application.

Figure 2:
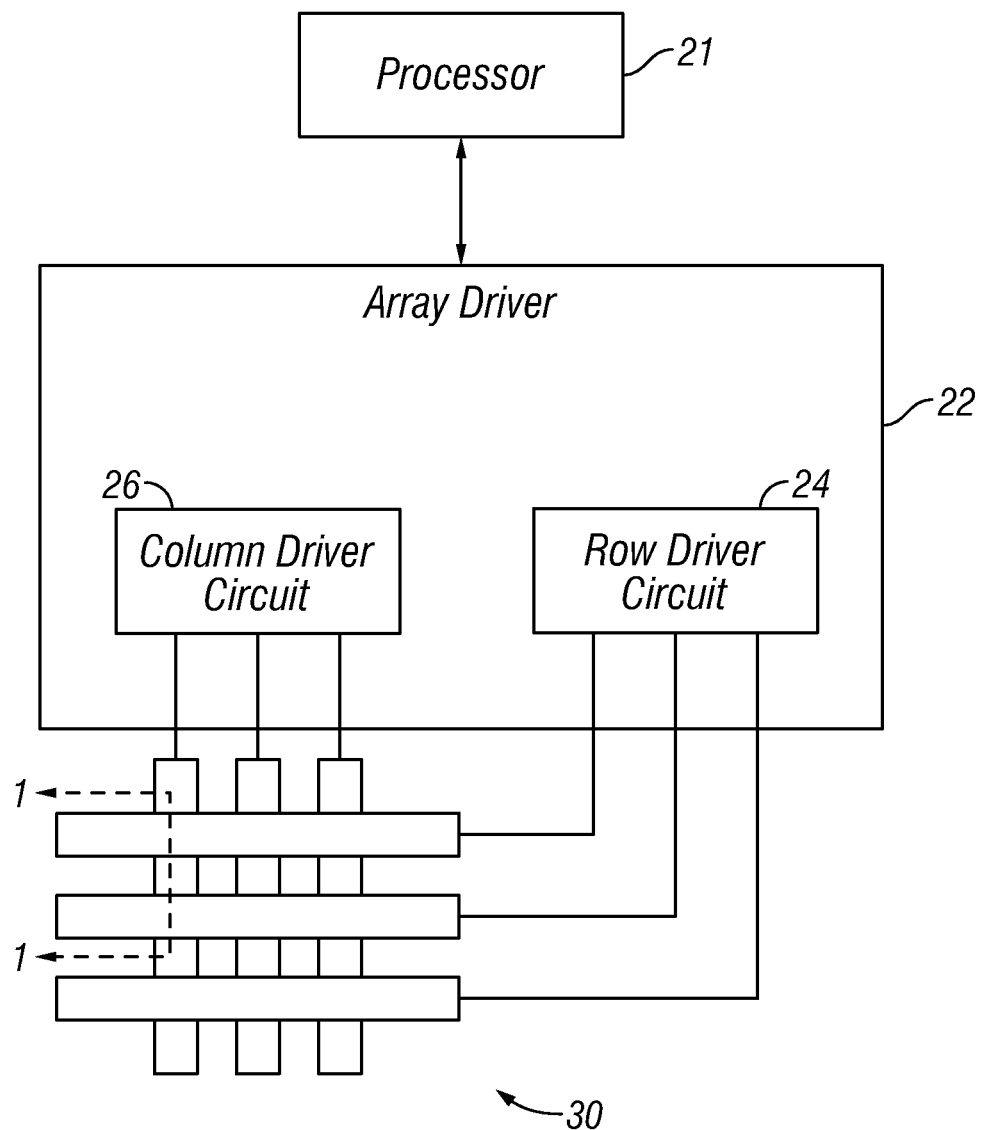
FIG. 2 is a system block diagram illustrating one embodiment of an electronic device incorporating a 3×3 interferometric modulator display.

FIG. 2 is a system block diagram illustrating one embodiment of an electronic device that may incorporate interferometric modulators. The electronic device includes a processor 21 which may be any general purpose single- or multi-chip microprocessor such as an ARM®, Pentium®, 8051, MIPS®, Power PC®, or ALPHA®, or any special purpose microprocessor such as a digital signal processor, microcontroller, or a programmable gate array. As is conventional in the art, the processor 21 may be configured to execute one or more software modules. In addition to executing an operating system, the processor may be configured to execute one or more software applications, including a web browser, a telephone application, an email program, or any other software application.

In one embodiment, the processor 21 is also configured to communicate with an array driver 22. In one embodiment, the array driver 22 includes a row driver circuit 24 and a column driver circuit 26 that provide signals to a display array or panel 30. The cross section of the array illustrated in FIG. 1 is shown by the lines 1-1 in FIG. 2. Note that although FIG. 2 illustrates a 3×3 array of interferometric modulators for the sake of clarity, the display array 30 may contain a very large number of interferometric modulators, and may have a different number of interferometric modulators in rows than in columns (e.g., 300 pixels per row by 190 pixels per column).

Figures 3, 4:
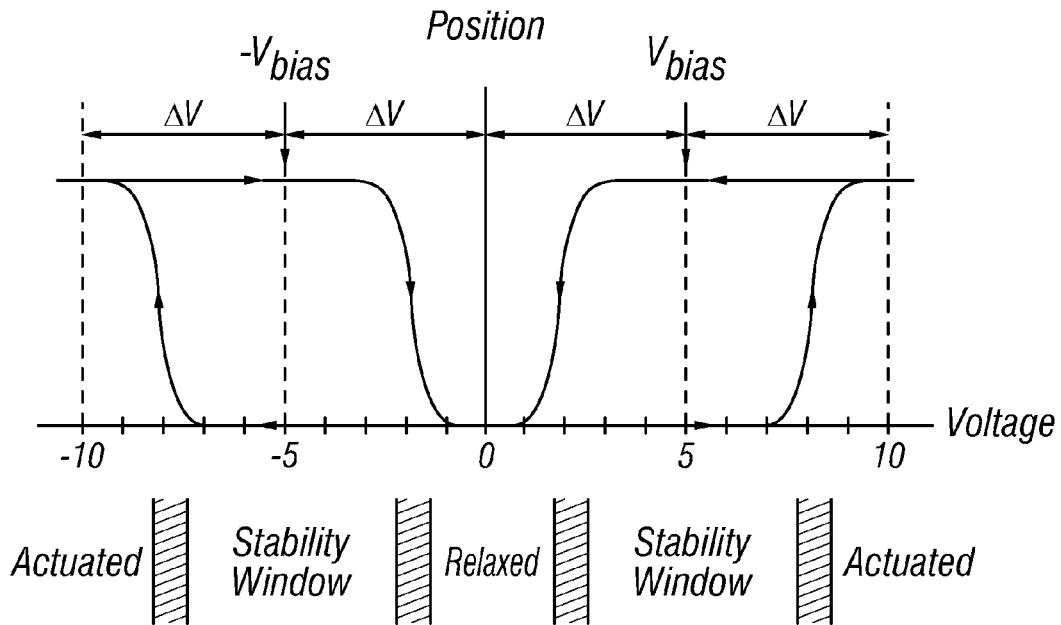
FIG. 3 is a diagram of movable mirror position versus applied voltage for one exemplary embodiment of an interferometric modulator of FIG. 1.
FIG. 4 is an illustration of a set of row and column voltages that may be used to drive an interferometric modulator display.

FIG. 3 is a diagram of movable mirror position versus applied voltage for one exemplary embodiment of an interferometric modulator of FIG. 1. For MEMS interferometric modulators, the row/column actuation protocol may take advantage of a hysteresis property of these devices as illustrated in FIG. 3. An interferometric modulator may require, for example, a 10 volt potential difference to cause a movable layer to deform from the relaxed state to the actuated state. However, when the voltage is reduced from that value, the movable layer maintains its state as the voltage drops back below 10 volts. In the exemplary embodiment of FIG. 3, the movable layer does not relax completely until the voltage drops below 2 volts. There is thus a range of voltage, about 3 to 7 V in the example illustrated in FIG. 3, where there exists a window of applied voltage within which the device is stable in either the relaxed or actuated state. This is referred to herein as the "hysteresis window" or "stability window." For a display array having the hysteresis characteristics of FIG. 3, the row/column actuation protocol can be designed such that during row strobing, pixels in the strobed row that are to be actuated are exposed to a voltage difference of about 10 volts, and pixels that are to be relaxed are exposed to a voltage difference of close to zero volts. After the strobe, the pixels are exposed to a steady state or bias voltage difference of about 5 volts such that they remain in whatever state the row strobe put them in. After being written, each pixel sees a potential difference within the "stability window" of 3-7 volts in this example. This feature makes the pixel design illustrated in FIG. 1 stable under the same applied voltage conditions in either an actuated or relaxed pre-existing state. Since each pixel of the interferometric modulator, whether in the actuated or relaxed state, is essentially a capacitor formed by the fixed and moving reflective layers, this stable state can be held at a voltage within the hysteresis window with almost no power dissipation. Essentially no current flows into the pixel if the applied potential is fixed.

As described further below, in typical applications, a frame of an image may be created by sending a set of data signals (each having a certain voltage level) across the set of column electrodes in accordance with the desired set of actuated pixels in the first row. A row pulse is then applied to a first row electrode, actuating the pixels corresponding to the set of data signals. The set of data signals is then changed to correspond to the desired set of actuated pixels in a second row. A pulse is then applied to the second row electrode, actuating the appropriate pixels in the second row in accordance with the data signals. The first row of pixels are unaffected by the second row pulse, and remain in the state they were set to during the first row pulse. This may be repeated for the entire series of rows in a sequential fashion to produce the frame. Generally, the frames are refreshed and/or updated with new image data by continually repeating this process at some desired number of frames per second. A wide variety of protocols for driving row and column electrodes of pixel arrays to produce image frames may be used.

FIGS. 4 and 5 illustrate one possible actuation protocol for creating a display frame on the 3×3 array of FIG. 2. FIG. 4 illustrates a possible set of column and row voltage levels that may be used for pixels exhibiting the hysteresis curves of FIG. 3. In the FIG. 4 embodiment, actuating a pixel involves setting the appropriate column to $-V_{bias}$, and the appropriate row to $+\Delta V$, which may correspond to −5 volts and +5 volts respectively Relaxing the pixel is accomplished by setting the appropriate column to $+V_{bias}$, and the appropriate row to the same $+\Delta V$, producing a zero volt potential difference across the pixel. In those rows where the row voltage is held at zero volts, the pixels are stable in whatever state they were originally in, regardless of whether the column is at $+V_{bias}$, or $-V_{bias}$. As is also illustrated in FIG. 4, voltages of opposite polarity than those described above can be used, e.g., actuating a pixel can involve setting the appropriate column to $+V_{bias}$, and the appropriate row to $-\Delta V$. In this embodiment, releasing the pixel is accomplished by setting the appropriate column to $-V_{bias}$, and the appropriate row to the same $-\Delta V$, producing a zero volt potential difference across the pixel.

Figure 5A:
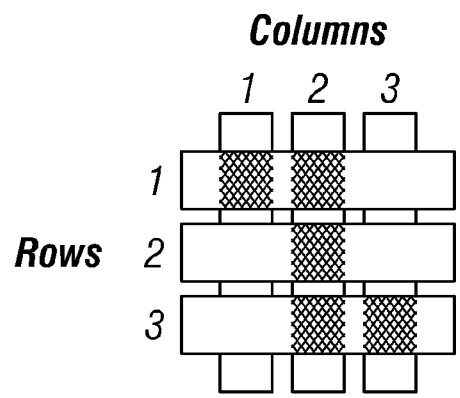
FIGS. 5A and 5B illustrate one exemplary timing diagram for row and column signals that may be used to write a frame of display data to the 3×3 interferometric modulator display of FIG. 2.
Figure 5B:
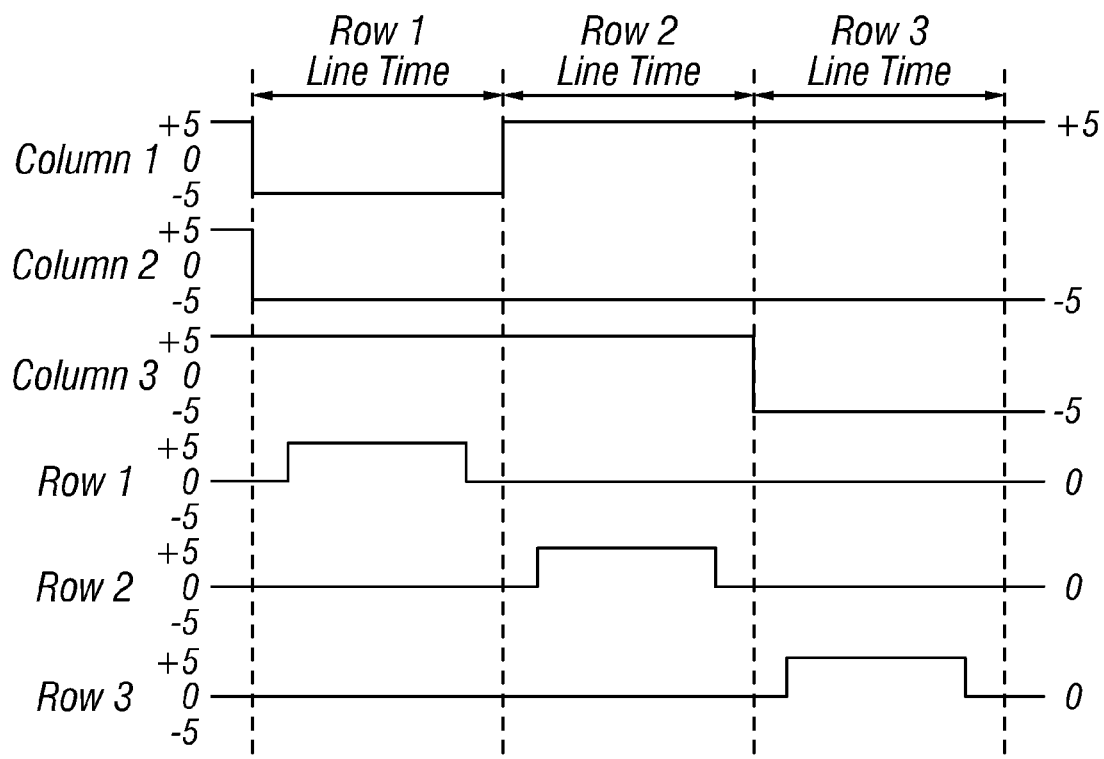

FIG. 5B is a timing diagram showing a series of row and column signals applied to the 3×3 array of FIG. 2 which will result in the display arrangement illustrated in FIG. 5A, where actuated pixels are non-reflective. Prior to writing the frame illustrated in FIG. 5A, the pixels can be in any state, and in this example, all the rows are initially at 0 volts, and all the columns are at +5 volts. With these applied voltages, all pixels are stable in their existing actuated or relaxed states.

In the FIG. 5A frame, pixels (1,1), (1,2), (2,2), (3,2) and (3,3) are actuated. To accomplish this, during a "line time" for row 1, columns 1 and 2 are set to −5 volts, and column 3 is set to +5 volts. This does not change the state of any pixels, because all the pixels remain in the 3-7 volt stability window. Row 1 is then strobed with a pulse that goes from 0, up to 5 volts, and back to zero. This actuates the (1,1) and (1,2) pixels and relaxes the (1,3) pixel. No other pixels in the array are affected. To set row 2 as desired, column 2 is set to −5 volts, and columns 1 and 3 are set to +5 volts. The same strobe applied to row 2 will then actuate pixel (2,2) and relax pixels (2,1) and (2,3). Again, no other pixels of the array are affected. Row 3 is similarly set by setting columns 2 and 3 to −5 volts, and column 1 to +5 volts. The row 3 strobe sets the row 3 pixels as shown in FIG. 5A. After writing the frame, the row potentials are zero, and the column potentials can remain at either +5 or −5 volts, and the display is then stable in the arrangement of FIG. 5A. The same procedure can be employed for arrays of dozens or hundreds of rows and columns. The timing, sequence, and levels of voltages used to perform row and column actuation can be varied widely within the general principles outlined above, and the above example is exemplary only, and any actuation voltage method can be used with the systems and methods described herein.

Figure 6A:
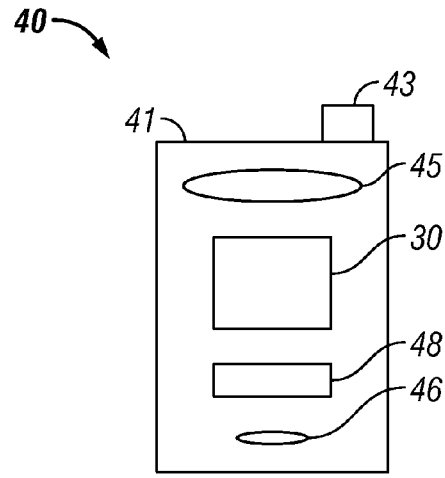
FIGS. 6A and 6B are system block diagrams illustrating an embodiment of a visual display device comprising a plurality of interferometric modulators.
Figure 6B:
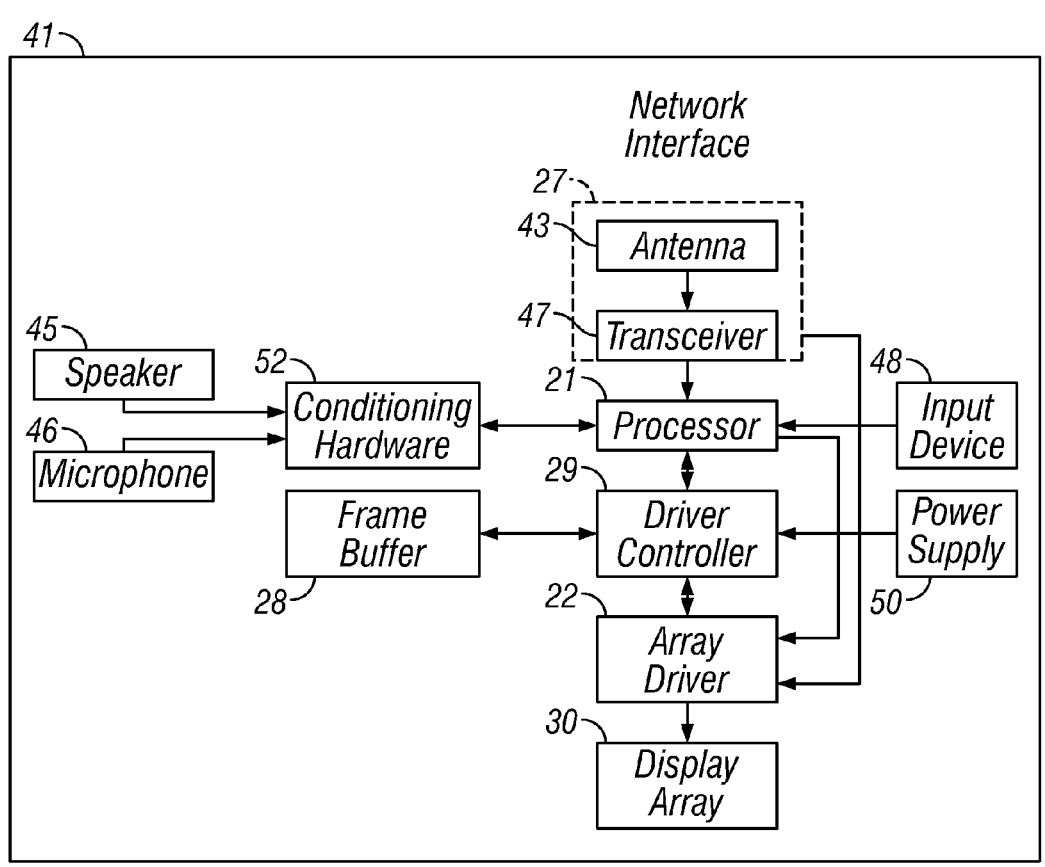

FIGS. 6A and 6B are system block diagrams illustrating an embodiment of a display device 40. The display device 40 can be, for example, a cellular or mobile telephone. However, the same components of display device 40 or slight variations thereof are also illustrative of various types of display devices such as televisions and portable media players.

The display device 40 includes a housing 41, a display 30, an antenna 43, a speaker 45, an input device 48, and a microphone 46. The housing 41 is generally formed from any of a variety of manufacturing processes, including injection molding, and vacuum forming. In addition, the housing 41 may be made from any of a variety of materials, including but not limited to plastic, metal, glass, rubber, and ceramic, or a combination thereof. In one embodiment the housing 41 includes removable portions (not shown) that may be interchanged with other removable portions of different color, or containing different logos, pictures, or symbols.

The display 30 of exemplary display device 40 may be any of a variety of displays, including a bi-stable display, as described herein. In other embodiments, the display 30 includes a flat-panel display, such as plasma, EL, OLED, STN LCD, or TFT LCD as described above, or a non-flat-panel display, such as a CRT or other tube device. However, for purposes of describing the present embodiment, the display 30 includes an interferometric modulator display, as described herein.

The components of one embodiment of exemplary display device 40 are schematically illustrated in FIG. 6B. The illustrated exemplary display device 40 includes a housing 41 and can include additional components at least partially enclosed therein. For example, in one embodiment, the exemplary display device 40 includes a network interface 27 that includes an antenna 43 which is coupled to a transceiver 47. The transceiver 47 is connected to a processor 21, which is connected to conditioning hardware 52. The conditioning hardware 52 may be configured to condition a signal (e.g. filter a signal). The conditioning hardware 52 is connected to a speaker 45 and a microphone 46. The processor 21 is also connected to an input device 48 and a driver controller 29. The driver controller 29 is coupled to a frame buffer 28, and to an array driver 22, which in turn is coupled to a display array 30. A power supply 50 provides power to all components as required by the particular exemplary display device 40 design.

The network interface 27 includes the antenna 43 and the transceiver 47 so that the exemplary display device 40 can communicate with one ore more devices over a network. In one embodiment the network interface 27 may also have some processing capabilities to relieve requirements of the processor 21. The antenna 43 is any antenna for transmitting and receiving signals. In one embodiment, the antenna transmits and receives RF signals according to the IEEE 802.11 standard, including IEEE 802.11(a), (b), or (g). In another embodiment, the antenna transmits and receives RF signals according to the BLUETOOTH standard. In the case of a cellular telephone, the antenna is designed to receive CDMA, GSM, AMPS, W-CDMA, or other known signals that are used to communicate within a wireless cell phone network. The transceiver 47 pre-processes the signals received from the antenna 43 so that they may be received by and further manipulated by the processor 21. The transceiver 47 also processes signals received from the processor 21 so that they may be transmitted from the exemplary display device 40 via the antenna 43.

In an alternative embodiment, the transceiver 47 can be replaced by a receiver. In yet another alternative embodiment, network interface 27 can be replaced by an image source, which can store or generate image data to be sent to the processor 21. For example, the image source can be a digital video disc (DVD) or a hard-disc drive that contains image data, or a software module that generates image data.

Processor 21 generally controls the overall operation of the exemplary display device 40. The processor 21 receives data, such as compressed image data from the network interface 27 or an image source, and processes the data into raw image data or into a format that is readily processed into raw image data. The processor 21 then sends the processed data to the driver controller 29 or to frame buffer 28 for storage. Raw data typically refers to the information that identifies the image characteristics at each location within an image. For example, such image characteristics can include color, saturation, and gray-scale level.

In one embodiment, the processor 21 includes a microcontroller, CPU, or logic unit to control operation of the exemplary display device 40. Conditioning hardware 52 generally includes amplifiers and filters for transmitting signals to the speaker 45, and for receiving signals from the microphone 46. Conditioning hardware 52 may be discrete components within the exemplary display device 40, or may be incorporated within the processor 21 or other components.

The driver controller 29 takes the raw image data generated by the processor 21 either directly from the processor 21 or from the frame buffer 28 and reformats the raw image data appropriately for high speed transmission to the array driver 22. Specifically, the driver controller 29 reformats the raw image data into a data flow having a raster-like format, such that it has a time order suitable for scanning across the display array 30. Then the driver controller 29 sends the formatted information to the array driver 22. Although a driver controller 29, such as a LCD controller, is often associated with the system processor 21 as a stand-alone Integrated Circuit (IC), such controllers may be implemented in many ways. They may be embedded in the processor 21 as hardware, embedded in the processor 21 as software, or fully integrated in hardware with the array driver 22.

Typically, the array driver 22 receives the formatted information from the driver controller 29 and reformats the video data into a parallel set of waveforms that are applied many times per second to the hundreds and sometimes thousands of leads coming from the display's x-y matrix of pixels.

In one embodiment, the driver controller 29, array driver 22, and display array 30 are appropriate for any of the types of displays described herein. For example, in one embodiment, driver controller 29 is a conventional display controller or a bi-stable display controller (e.g., an interferometric modulator controller). In another embodiment, array driver 22 is a conventional driver or a bi-stable display driver (e.g., an interferometric modulator display). In one embodiment, a driver controller 29 is integrated with the array driver 22. Such an embodiment is common in highly integrated systems such as cellular phones, watches, and other small area displays. In yet another embodiment, display array 30 is a typical display array or a bi-stable display array (e.g., a display including an array of interferometric modulators).

The input device 48 allows a user to control the operation of the exemplary display device 40. In one embodiment, input device 48 includes a keypad, such as a QWERTY keyboard or a telephone keypad, a button, a switch, a touch-sensitive screen, a pressure- or heat-sensitive membrane. In one embodiment, the microphone 46 is an input device for the exemplary display device 40. When the microphone 46 is used to input data to the device, voice commands may be provided by a user for controlling operations of the exemplary display device 40.

Power supply 50 can include a variety of energy storage devices as are well known in the art. For example, in one embodiment, power supply 50 is a rechargeable battery, such as a nickel-cadmium battery or a lithium ion battery. In another embodiment, power supply 50 is a renewable energy source, a capacitor, or a solar cell, including a plastic solar cell, and solar-cell paint. In another embodiment, power supply 50 is configured to receive power from a wall outlet.

In some implementations control programmability resides, as described above, in a driver controller which can be located in several places in the electronic display system. In some cases control programmability resides in the array driver 22. The above-described optimization may be implemented in any number of hardware and/or software components and in various configurations.

Figure 7A:
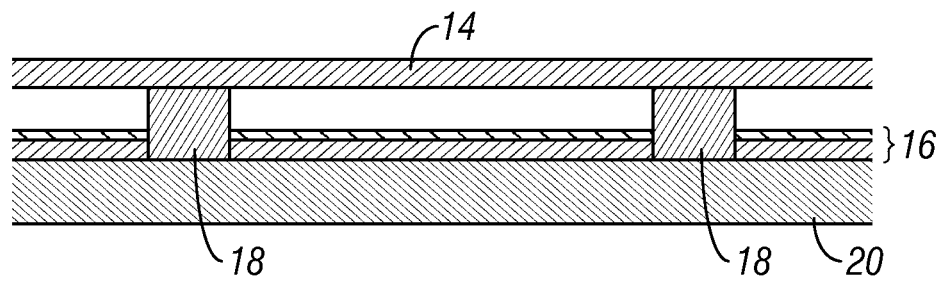
FIG. 7A is a cross section of the device of FIG. 1.
Figure 7B:
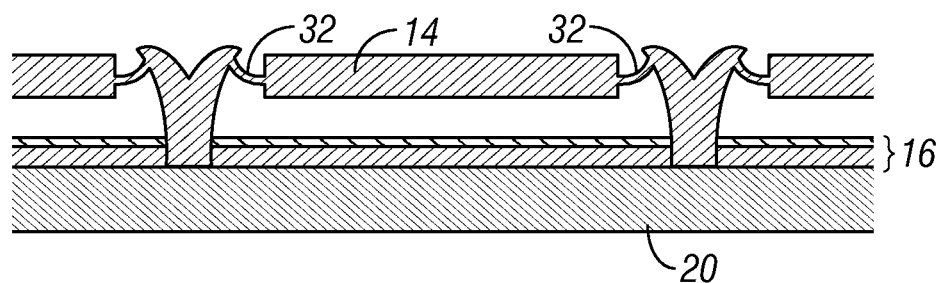
FIG. 7B is a cross section of an alternative embodiment of an interferometric modulator.
Figure 7C:
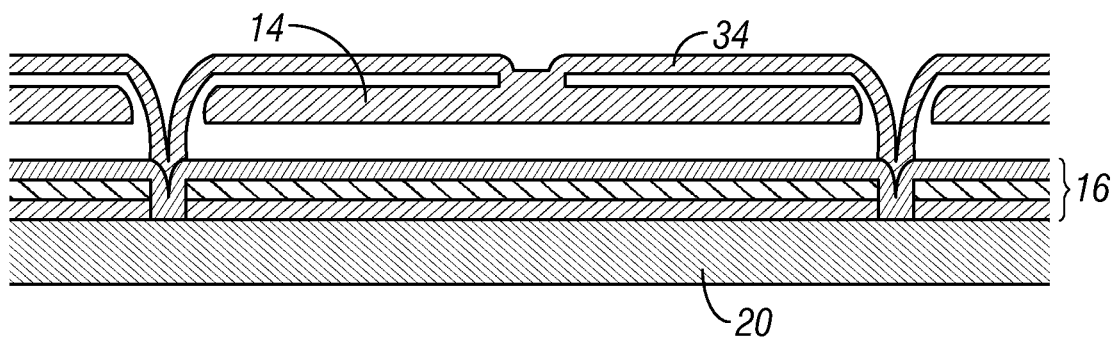
FIG. 7C is a cross section of another alternative embodiment of an interferometric modulator.
Figure 7D:
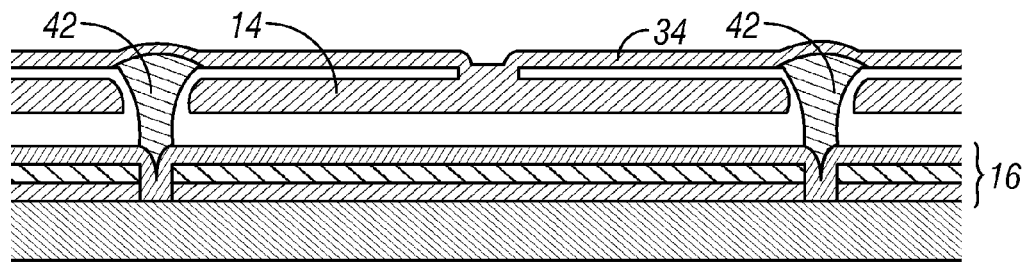
FIG. 7D is a cross section of yet another alternative embodiment of an interferometric modulator.
Figure 7E:
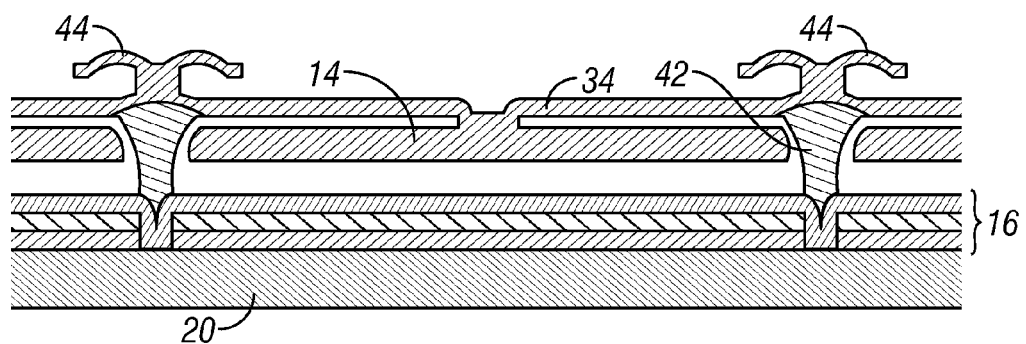
FIG. 7E is a cross section of an additional alternative embodiment of an interferometric modulator.

The details of the structure of interferometric modulators that operate in accordance with the principles set forth above may vary widely. For example, FIGS. 7A-7E illustrate five different embodiments of the movable reflective layer 14 and its supporting structures. FIG. 7A is a cross section of the embodiment of FIG. 1, where a strip of metal material 14 is deposited on orthogonally extending supports 18. In FIG. 7B, the moveable reflective layer 14 of each interferometric modulator is square or rectangular in shape and attached to supports at the corners only, on tethers 32. In FIG. 7C, the moveable reflective layer 14 is square or rectangular in shape and suspended from a deformable layer 34, which may comprise a flexible metal. The deformable layer 34 connects, directly or indirectly, to the substrate 20 around the perimeter of the deformable layer 34. These connections are herein referred to as support posts. The embodiment illustrated in FIG. 7D has support post plugs 42 upon which the deformable layer 34 rests. The movable reflective layer 14 remains suspended over the gap, as in FIGS. 7A-7C, but the deformable layer 34 does not form the support posts by filling holes between the deformable layer 34 and the optical stack 16. Rather, the support posts are formed of a planarization material, which is used to form support post plugs 42. The embodiment illustrated in FIG. 7E is based on the embodiment shown in FIG. 7D, but may also be adapted to work with any of the embodiments illustrated in FIGS. 7A-7C as well as additional embodiments not shown. In the embodiment shown in FIG. 7E, an extra layer of metal or other conductive material has been used to form a bus structure 44. This allows signal routing along the back of the interferometric modulators, eliminating a number of electrodes that may otherwise have had to be formed on the substrate 20.

In embodiments such as those shown in FIG. 7, the interferometric modulators function as direct-view devices, in which images are viewed from the front side of the transparent substrate 20, the side opposite to that upon which the modulator is arranged. In these embodiments, the reflective layer 14 optically shields the portions of the interferometric modulator on the side of the reflective layer opposite the substrate 20, including the deformable layer 34. This allows the shielded areas to be configured and operated upon without negatively affecting the image quality. For example, such shielding allows the bus structure 44 in FIG. 7E, which provides the ability to separate the optical properties of the modulator from the electromechanical properties of the modulator, such as addressing and the movements that result from that addressing. This separable modulator architecture allows the structural design and materials used for the electromechanical aspects and the optical aspects of the modulator to be selected and to function independently of each other. Moreover, the embodiments shown in FIGS. 7C-7E have additional benefits deriving from the decoupling of the optical properties of the reflective layer 14 from its mechanical properties, which are carried out by the deformable layer 34. This allows the structural design and materials used for the reflective layer 14 to be optimized with respect to the optical properties, and the structural design and materials used for the deformable layer 34 to be optimized with respect to desired mechanical properties.

The selective absorption and reflection of light by an interferometric modulator can be used in connection with methods of detecting small chemical changes in a variety of materials. In this way, the interferometric modulator may be configured in to act as an environmental condition monitoring device. Depending on the particular configuration of the device and depending on the environmental conditions to which the device is exposed, the optical properties of the device change significantly.

In embodiments such as those shown in FIG. 8, an environmental reactive layer 804 is disposed on an optical enhancement layer 808. In one embodiment the optical enhancement layer 808 may comprise a dielectric layer 806 disposed on a reflector layer 807. The optical enhancement layer 808 may further be disposed on a glass substrate (not shown). In one embodiment, the environmental reactive layer 804 forms part of the interferometric cavity of the interferometric modulator 800. This environmental condition monitoring device 800 can be used to detect exposure to certain environmental conditions. FIG. 8a shows the device 800 in its initial configuration before exposure to an environmental condition. When the environmental reactive layer 804 is exposed to a pre-determined environmental condition, it begins to chemically modify. As seen in FIG. 8b, the chemical modification may not be uniform across the surface of the environmental reactive layer 804. The chemical modification causes part of the environmental reactive layer 804 to convert to a chemically modified layer 812. The change in the environmental reactive layer 804 causes an overall change in the optical properties of the device 800 as the optical properties of the environmental reactive layer 804 and the chemically modified layer 812 are different. The optical enhancement layer 808 enhances the change in optical properties of the device 800 compared to the change in optical properties of the environmental reactive layer 804 itself making the device 800 highly sensitive to exposure to a pre-determined environmental condition.

Figure 9:
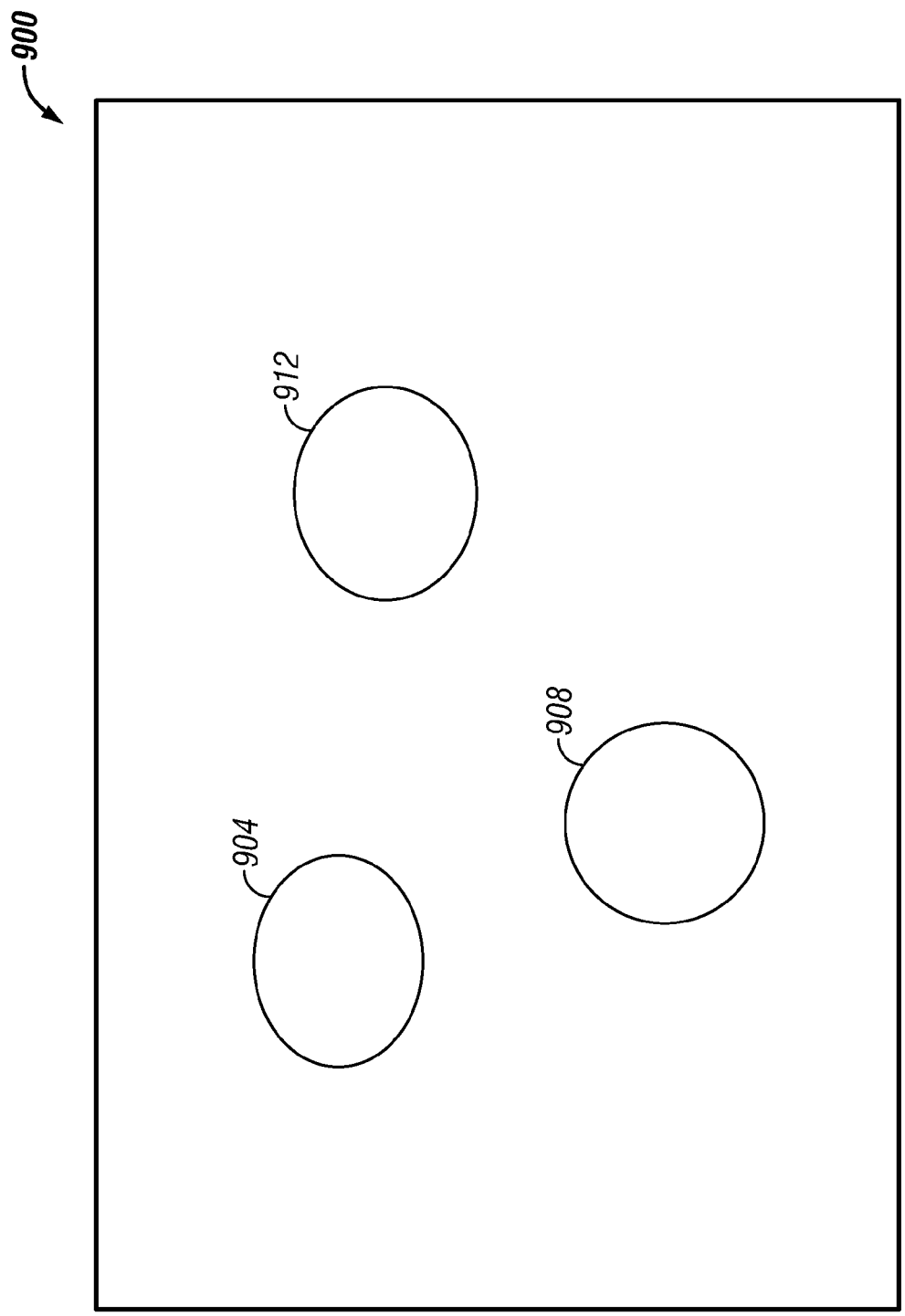
FIG. 9 is an illustration of a top view of an embodiment of the environmental condition detection device illustrating spatially non-uniform chemical modification.

FIG. 9 shows a top plan view of an embodiment of the environmental condition monitoring device 800 of FIG. 8. In the embodiment shown in FIG. 9, the environmental reactive layer 900 does not always chemically modify uniformly across the entire surface. In this case, some areas 904 of the environmental reactive layer 900 may have a different composition than other areas 908, 912. In some areas 904, the environmental layer chemically modifies from the top of the layer down to the bottom of the layer. These areas 904 appear as pinholes or bright spots surrounded by dark area. It is possible to compare the area 904 of the layer containing pinholes to the total area of the layer 900 to implicitly estimate the amount of water that has reacted with the environmental reactive layer 900. Smaller levels of chemical modification do not appear as pinholes, but may still have a change in optical properties, such as areas 908 and 912. Depending on the configuration of the device, the sensitivity of the detection device 800 to such changes is adjusted.

In one embodiment, the high sensitivity of the device 800 allows for unaccelerated detection of extremely low permeation of gas into a package even when a small total area for the environmental reactive layer 804 is chosen. Further, the high sensitivity allows for detection of sub-nm changes in composition and/or thickness of the environmental reactive layer 804.

In one embodiment, the optical enhancement layer 808 comprises materials chosen to create an optical resonance in the environmental reactive layer 804. The environmental reactive layer 804 acts as an optical absorber layer in this embodiment. The environmental reactive layer 804 may be a metal (e.g., Al, Ca, Ni). The thickness of the environmental reactive layer 804 may be chosen to be less than a skin depth of the metal chosen. The skin depth of the metal is the depth to which electromagnetic radiation (e.g., light) can penetrate the surface of the metal. Further, the thickness of the environmental reactive layer 804 may be chosen to act as an absorber in conjunction with the optical enhancement layer 808.

In an embodiment, the optical enhancement layer 808 comprises a dielectric layer 806 and a reflector layer 807. The reflector layer 807 may comprise a metal (e.g., Al). The thickness of the reflector layer 807 may be greater than a skin depth of the metal chosen. Accordingly, the reflector layer 807 reflects light efficiently. Further, the thickness of the dielectric layer may be chosen such that the device 800 exhibits certain optical properties. For example, the thickness chosen for the dielectric layer 806 may shift the reflectivity spectrum of the device 800 with respect to wavelength as discussed below with respect to FIG. 10.

As discussed above, in one embodiment of FIG. 8, the environmental reactive layer 804 is a metal. Depending on the metal chosen, the environmental reactive layer 804 responds to exposure to a pre-determined environmental condition. For instance, in one embodiment, calcium is chosen as the environmental reactive layer 804. Calcium readily reacts with water, and therefore can be used to respond to exposure to water. As the calcium reacts with water it is converted into a dielectric, forming the chemically modified layer 812. This causes the height of the layer 804 of calcium to change as more material reacts. The process continues as long as moisture is present and calcium remains.

In other exemplary embodiments, a semiconductor such as silicon may be chosen for the environmental reactive layer 804. Other exemplary materials include silica, aluminum, nickel, etc.

Figure 10:
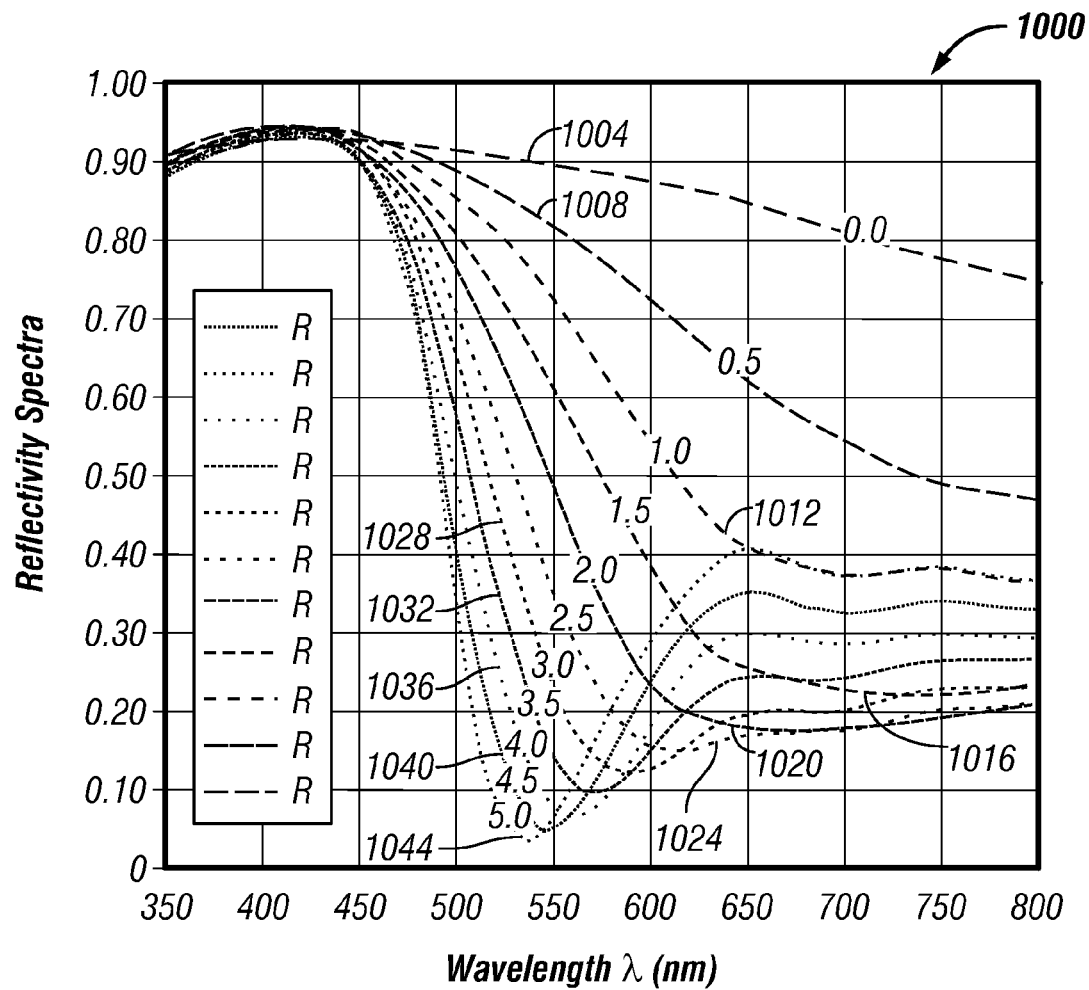
FIG. 10 is graph of the reflectivity spectrum of an embodiment of the environmental condition detection device.

In the embodiment of FIG. 8, some of the environmental reactive layer's 804 optical properties change as it reacts with the environment. Optical properties such as chromaticity, reflectivity, color, saturation, and/or hue, etc. may then be monitored to detect the presence or exposure to the predetermined environmental condition. In an exemplary embodiment, the environmental reactive layer 804 includes calcium, a highly light absorbing metal. When calcium reacts with water it is converted into a dielectric, forming the chemically modified layer 812, which has almost no optical absorption. The exposure of the environmental reactive layer 804 to water, therefore, causes the reflectivity spectrum of the environmental reactive layer 804 to change. Though the reflectivity spectrum of the environmental reactive layer 804 itself may not change greatly, the overall optical response of the device 800 as seen in FIG. 10 changes significantly due to the configuration of the interferometric modulator 800, which includes an environmental reactive layer 804 deposited on an optical enhancement layer 808. The optical properties of the device 800 change significantly with small changes to the environmental reactive layer 804. In one embodiment, the optical properties of the device 800 have a large sensitivity to the presence of minute amounts of an environmental condition, for example, a gas species (e.g. water, oxygen), which causes a small change in the environmental reactive layer 804.

FIG. 10 shows reflectivity spectra for an embodiment of the device 800 with an initial configuration of 5 nm of aluminum as the environmental reactive layer 804, 133 nm of SiO$_2$ as the dielectric layer 806, and 100 nm of aluminum as the reflector layer 807, which is further disposed on a glass substrate. Each numbered line 1004-1044 of the graph 1000 represents a different level of chemical modification of the environmental reactive layer 804. Each line 1004-1044 plots the reflectivity at different wavelengths of light for a particular configuration of the device 800, each configuration having a different thickness remaining for the environmental reactive layer 804. For example, line 1004 corresponds to a thickness of 0 nm of Al left, while line 1044 corresponds to a thickness of 5 nm of Al left of the environmental reactive layer 804. In the embodiment of FIG. 10, the material used for the optical enhancement layer 808 remains constant, while the level of chemical modification of the environmental reactive layer 804 changes between each numbered line 1004-1044. As seen in FIG. 10, the change in reflectivity between each line 1004-1044 is dependent on the wavelength of light incident to the device 800. In order to better monitor exposure of the device 800 to an environmental condition, a wavelength of light having a high delta value for varying thicknesses of the environmental reactive layer 804 may be selected for analysis when measuring the effect of the environment on the environmental reactive layer 804. For example, in the embodiment of FIG. 10, a wavelength of 538 nm may be selected for analysis because of the high delta value between each lines 1004-1044 at that wavelength.

One of ordinary skill in the art will recognize that changing the initial thickness and/or material of the dielectric layer 806, the reflector layer 807, and/or the environmental reactive layer 804, and/or changing the exposure to an environmental condition changes the reflectivity response of the device 800. For example, changing the thickness of the dielectric layer 806 may shift the lines 1004-1044 along the x-axis (wavelength). Therefore, the wavelength of light having a high delta value for varying thicknesses of the environmental reactive layer 804 may be shifted. Accordingly, the thickness of the dielectric layer 806 may be selected to choose a particular wavelength of light for analysis. In one embodiment, the wavelength of light chosen for analysis is based on the optimal wavelength for detection by monitoring equipment used to detect the change in reflectivity.

Figure 11:
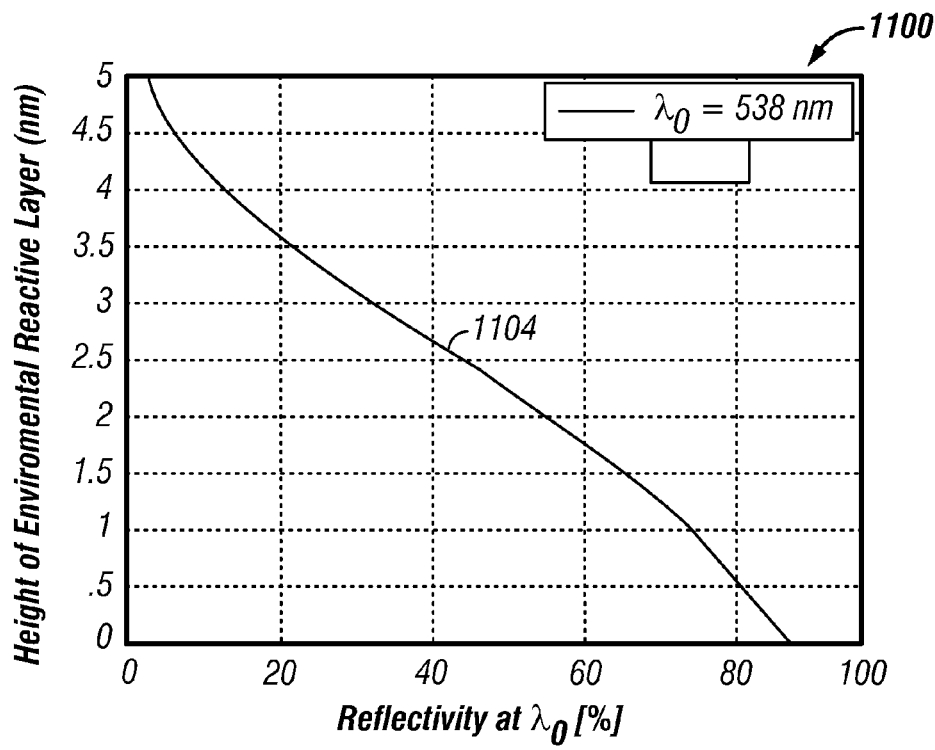
FIG. 11 is a graph of the reflectivity of an embodiment of the environmental condition detection device at an exemplary wavelength.

FIG. 11 shows the reflectivity of an embodiment of the environmental condition monitoring device 800 with an initial configuration of 5 nm of aluminum as the environmental reactive layer 804, 133 nm of SiO$_2$ as the dielectric layer 806, and 100 nm of aluminum as the reflector layer 807, which is further disposed on a glass substrate. In the embodiment of FIG. 11, the reflectivity of the device 800 is measured at a wavelength of 538 nm. One of ordinary skill in the art will recognize that changing the optical enhancement layer 808, the environmental reactive layer 804, or the exposure to an environmental condition changes the reflectivity response of the device 800. One of ordinary skill in the art will also recognize that reflectivity may be measured at other wavelengths. As seen in the graph 1100, the plot of reflectivity 1104 may change significantly as the level of chemical modification of the environmental layer changes. In one exemplary embodiment, the level of chemical modification of the environmental reactive layer 804 refers to a remaining height of the layer 804 measured between the top of the optical enhancement layer 808 to bottom of the chemically modified layer 812. One of ordinary skill in the art will recognize that other optical properties (e.g., chromaticity) of the device 800 may change as the level of chemical modification of the environmental layer changes. Accordingly, these other optical properties may be measured to determine the level of chemical modification. For example, one may use a colorimeter or other equipment to measure the level of chemical modification if equipment for a full spectral response is unavailable.

Figure 12:
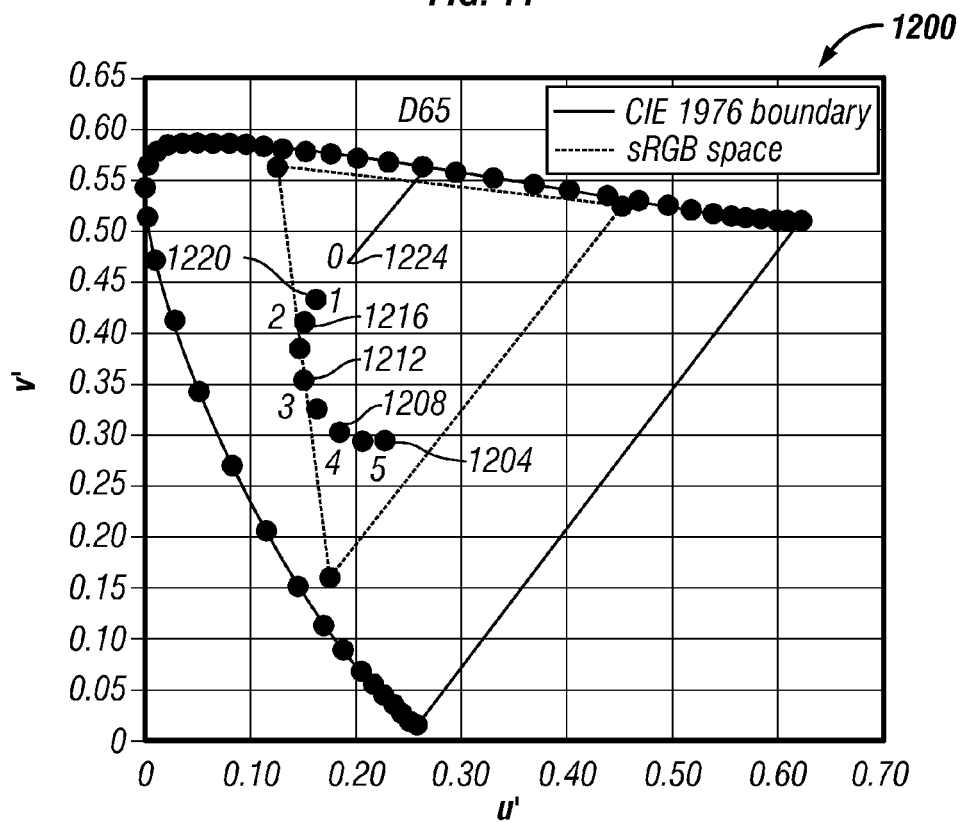
FIG. 12 is a chromaticity diagram of an embodiment of the environmental condition detection device.

In another embodiment, the chromaticity of the device 800 may change as the level of chemical modification of the environmental reactive layer 804 changes. FIG. 12 shows a chromaticity diagram 1200 of an embodiment of the device 800 with an initial configuration of 5 nm of aluminum as the environmental reactive layer 804, 133 nm of SiO$_2$ as the dielectric layer 806, and 100 nm of aluminum as the reflector layer 807, which is further disposed on a glass substrate. One of ordinary skill in the art will recognize that changing the optical enhancement layer 808, the environmental reactive layer 804, or the exposure to an environmental condition changes the chromaticity of the device 800. Each numbered point 1204-1224 represents the chromaticity of the device 800 at a different level of chemical modification. Point 1204 refers to the chromaticity of the device 800 at the starting point of 5 nm of Al left of the environmental reactive layer 804. Each successive point 1208-1224 refers to the chromaticity of the device 800 with a different amount of environmental layer 804 left. Point 1208 refers to the chromaticity of the device 800 at 4 nm of Al left of the environmental reactive layer 804, point 1212 refers to 3 nm of Al left, point 1216 refers to 2 nm of Al left, point 1220 refers to 1 nm of Al left, and point 1224 refers to no Al left of the environmental reactive layer 804. In one embodiment, each numbered point 1204-1224 corresponds to a remaining thickness of the environmental reactive layer measured in nanometers. As seen in FIG. 12, the chromaticity of the device 800 changes significantly as the level of chemical modification of the environmental reactive layer 804 changes from points 1204 through 1224.

Figure 13:
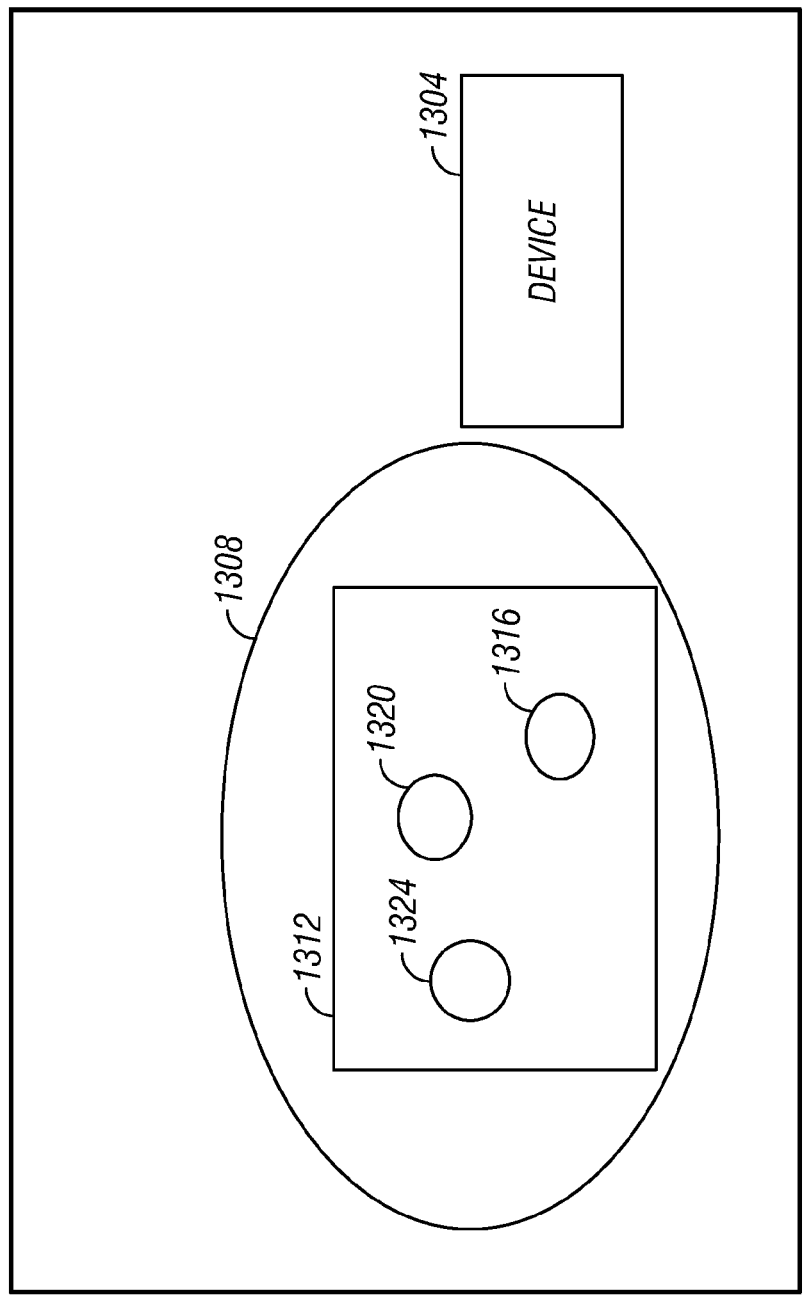
FIG. 13 is an illustration of a system for detecting exposure of a high performance device to an environmental condition.

FIG. 13 is an embodiment of the environmental condition monitoring device 800 being used in a package 1300 to detect the exposure of the inside of the package 1300 to a pre-determined environmental condition. The package may also include a second device 1304 (e.g. MEMS device (e.g., as shown in FIG. 1 and described herein), OLED, LED, LCD, etc.) which is sensitive to exposure to the pre-determined environmental condition. In one embodiment, the package includes a window or transparent covering 1308 for viewing the top of the environmental condition monitoring device 1312 so the optical properties can be measured without opening the package. In this manner, the exposure of the second device 1304 to a pre-determined environmental condition can be determined by monitoring the change in optical properties of the monitoring device 1312, which is exposed to the same environmental conditions.

In one embodiment, the device 800 is manufactured according to the process 1400 of FIG. 14. The configuration of the device 800 depends on the manufacturing process 1400. A first step 1404 of the process 1400 is for the manufacturer to select a material and initial thickness for the environmental reactive layer 804. The selection of both the type of material and the amount of material affects the overall functionality of the device. Depending on the desired sensitivity and size of the device 800 and the environmental condition being monitored, the material for the environmental reactive layer 804 is chosen by the manufacturer. As described with regards to the embodiment of FIG. 8, materials such as calcium, aluminum, nickel, silicon, silica, etc. may be chosen for the environmental reactive layer 804. In one embodiment, the environmental reactive layer 804 is chosen to be a material with a thickness that initially has a high optical absorption, e.g., metal. Further, the material for the embodiment may be chosen such that when the environmental reactive layer 804 is exposed to the environmental condition, it chemically modifies to a layer 812 that has little to no optical absorption, e.g., a dielectric. One of ordinary skill in the art will note that several other materials which are known to react to certain environmental conditions, such as a particular gas species, may also be used for the environmental reactive layer 804.

A particular thickness for the environmental reactive layer 804 may be chosen by the manufacturer in the first step 1404 to enhance the optical response to changes in the environmental layer 804. In one embodiment, the initial thickness of the environmental reactive layer 804 may be chosen to be less than a skin depth of the metal chosen as described above with respect to FIG. 8. In another embodiment the initial thickness of the environmental reactive layer 804 is about 5 nm. In a yet another embodiment the initial thickness is chosen to be between 0 and 10 nm, e.g. 1 nm, 2 nm, 3 nm, 4 nm, 5 nm, 6 nm, 7 nm, 8 nm, 9 nm. In a further embodiment the thickness is chosen between 3 and 7 nm e.g., 4 nm, 5 nm, 6 nm. In another embodiment the thickness may be chosen to be about 20 nm.

The surface area of the environmental reactive layer 804 may be also chosen by the manufacturer in first step 1404 according to desired sensitivity of the device 800 and overall size of the device 800. In an exemplary embodiment, the overall size of the device 800 is limited by the size of the package 1300 in which the device 800 is to be used as seen in FIG. 13. The optical properties of the device 800 may change differently depending on the surface area chosen for the environmental reactive layer 804. In some embodiments, a larger area may be more desirable as it is visible to the naked eye. In other embodiments, a smaller area may be more desirable where it fits in a package 1300 of limited size. In one embodiment the surface area is chosen to be about 5×5 mm. In another embodiment, the surface area is chosen to be about 0.3×0.3 mm.

Next, at step 1408, in process 1400 of manufacturing the device according to the embodiment of FIG. 14, material or materials for the optical enhancement layer 808 are selected. The selection of both the type of material and the amount of material affects the overall functionality of the device 800. Depending on the desired sensitivity and size of the device 800 and the environmental condition being monitored, the material for the optical enhancement layer 808 is chosen. Further depending on the material used for the environmental reactive layer 804 and/or a desired wavelength of light to be monitored, the material for the optical enhancement layer 808 is chosen. In one embodiment, the material and amount of optical enhancement layer 808 is chosen to create an optical resonance in the environmental reactive layer 804. In a second embodiment, the optical enhancement layer 808 is configured to produce a particular stack color (e.g. blue) in the device 800 to make it easy for a human observer to detect a change in the environmental reactive layer 804 without the use of measuring equipment. In another embodiment, the optical enhancement layer 808 is configured to produce a lowest reflection state in the device 800 to maximize signal detection by measuring equipment. In yet another embodiment the optical enhancement layer 808 is a dielectric enhanced metal reflector layer. In an exemplary embodiment the optical enhancement layer 808 includes SiO2 coated on aluminum forming a stack.

Further, in step 1408, the thickness of the optical enhancement layer 808 may be chosen by the manufacturer such that the device 800 has a desired optical response. In an embodiment, the thickness is chosen such that a desired wavelength of light is substantially absorbed in the environmental reactive layer 804. This is due to the concentration of the electric field of the desired wavelength in the environmental reactive layer 804 as light is incident. In this embodiment, the appearance of the device 800 changes as the thickness and/or composition of the environmental reactive layer 804 changes. The optical enhancement layer 808 is configured to enhance the optical properties of the environmental reactive layer 804. In one embodiment the optical enhancement layer 808 includes about 133 nm of SiO2 on top of about 100 nm of Al. Other materials and thicknesses known to persons of ordinary skill in the art to selectively reflect and absorb light may also be used.

Continuing to step 1416 of the manufacturing process of FIG. 14 is deposition of the environmental reactive layer 804 on the optical enhancement layer 808. In exemplary embodiments the deposition of the material may be achieved by chemical vapor deposition, atomic layer deposition, physical vapor deposition, or ion plating. Other methods of deposition of materials may also be used.

FIG. 15 describes a process 1500 of testing the optical properties of the device 800 in response to exposure to a pre-determined environmental condition. In exemplary embodiments, the steps of the testing process 1500 may be carried out by a human or by computer or other automated device. According to the process of manufacture 1400 of FIG. 14, a device 800 is configured to detect small changes in composition of the environmental reactive layer 804. In one embodiment, the device 800 is configured to significantly change optical response with a change of about 0.2 nm in the level of the environmental reactive layer 804. Such fine intervals allow for detection of about $10^{-11}$ grams of water for example in an embodiment using calcium deposited on SiO2 on top of Aluminum further on top of a glass substrate. The device 800 may be configured to detect even smaller changes in height, using materials and methods described. In another embodiment, the device 800 may be configured to detect sub-nm changes in the environmental reactive layer 804.

At step 1504, in process 1500, the device 800 is exposed to an environmental condition. As described with respect to FIG. 8, this causes the environmental reactive layer 804 to chemically modify and the optical properties of the device 800 to change. Next, at step 1508, the change in optical properties is monitored using measuring equipment. The measuring equipment, in one embodiment, is configured to measure reflectivity. The measuring equipment in exemplary embodiments includes a CCD camera, a fiber optic probe, a CMOS sensor or other known image sensor equipment. In one embodiment, a CCD camera can provide a spatial map of the color distribution and therefore a spatial map of the amount of environmental reactive layer 804 on a measured sample area. In another embodiment, measuring equipment may not be used as detection of exposure of the device 800 to an environmental condition is achieved by looking directly at the device 800. In the proceeding step 1512, the optical properties of the device 800 at a particular exposure level to an environmental condition may then be recorded. The process 1500 can be repeated at a decision step 1516 so that a data collection of the optical properties of the device 800 at many levels of exposure are recorded. If the decision is made to continue at decision step 1516, then steps 1504-1512 are repeated. Particularly in step 1504 the device 800 is further exposed to an environmental condition further causing the environmental reactive layer 804 to chemically modify. If the decision is made not to continue at the decision step 1516, the process ends. In one embodiment, the data may be stored in a database, as a chart, etc. In some embodiments a graph may be derived from the data.

Optical response properties of the device 800 and/or environmental reactive layer 804 may already be known and such data may not need to be gathered by the process of FIG. 15.

Figure 16:
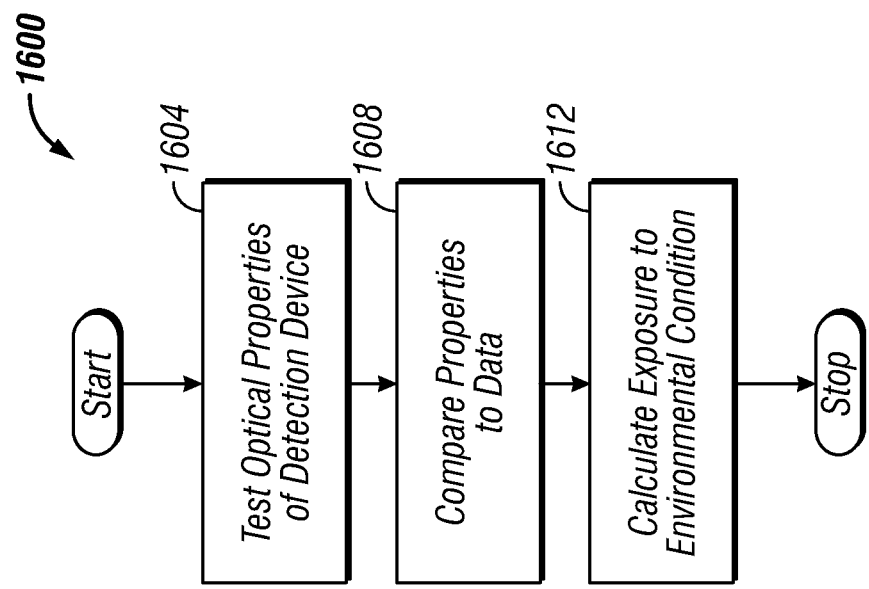
FIG. 16 is a flowchart of an embodiment of a process of testing the level of exposure of an embodiment of the environmental condition detection device to an environmental condition.

FIG. 16 describes the process 1600 by which the environmental condition monitoring device 800 is used by a user of the device to detect exposure to a pre-determined environmental condition. Similar to the step 1508 of monitoring change in optical properties of the device 800 in FIG. 15, the optical properties of the device 800 are measured using measuring equipment in the first step 1604. In the second step 1608, the results from the measuring equipment are then compared to the data collected in the process 1500 of FIG. 15 or known data for the optical response of the device 800. By examining such factors as the surface area of the environmental reactive layer 804, the materials used in composition of the device 800, the change in the optical response of the device 800 and the environmental condition being detected, a level of exposure to an environmental condition is calculated in a final step 1612. In this manner, exposure of the device 800 to an environmental condition can be determined.

In one embodiment of step 1608, the spatial map of the device 800 at a given moment can be compared to pre-collected data for the same configuration of device 800. In other exemplary embodiments of step 1608, the comparison may occur via a chart, or a data table, or other known means of relational graphing. The comparison can be done by hand or implemented by means of a computer or other data processing device. In exemplary embodiments, the processing device may be built into the same housing as the measuring equipment or may be separate.

In one embodiment, the device 800 is configured to change color at a specific amount of exposure to an environmental condition, where the change in color is detectable without measuring equipment (e.g., detectable with the naked eye). In this embodiment, step 1612 does not require a specific calculation, but rather the amount of exposure to an environmental condition is the amount at which the device 800 is configured to change color.

While the above processes 1400, 1500, and 1600 are described in the detailed description as including certain steps and are described in a particular order, it should be recognized that these processes may include additional steps or may omit some of the steps described. Further, each of the steps of the processes does not necessarily need to be performed in the order it is described. For example, step 1416 of process 1400 may be omitted, or step 1408 may be performed before step 1404.

In other exemplary embodiments, sensitivity of the device 800 to an environmental condition further depends on the rate at which the environmental reactive layer 804 reacts to the presence of an environmental condition. In such embodiments, the faster the rate of reaction, the sooner optical properties of device 800 change in response to exposure to an environmental condition.

The rate at which the composition of the environmental reactive layer 804 changes may depend on its exposure to certain conditions. For instance, in the embodiment where a metal is chosen for the environmental reactive layer 804, the pressure and/or temperature to which the environmental reactive layer 804 is exposed may change the rate at which it reacts with environmental conditions. Raising the temperature may increase the speed at which the layer 804 chemically modifies. In one embodiment, the device 800 is exposed to a particular temperature and/or pressure to adjust the rate at which the environmental reactive layer 804 reacts to the pre-determined environmental condition.

In the embodiment where a semi-conductor is chosen for the environmental reactive layer 804, the dose of light to which the environmental reactive layer 804 is exposed changes the rate at which it chemically modifies in the presence of a pre-determined environmental condition. For example, electron hole generation caused by absorption of light in a semiconductor can greatly accelerate chemical changes of the semiconductor material. In one embodiment, where silicon is used for the environmental reactive layer 804, this acceleration is based on electrochemical effects, such as the reactivity of silicon to oxidizing agents when light with energy larger than the electronic bandgap is incident on environmental reactive layer 804. In an exemplary embodiment, the environmental reactive layer 804 changes from an electrically conductive composition (optical absorbing) to chemically modified layer 812, an insulator composition (less optical absorbing) at a faster rate when exposed to a higher does of light.

In one embodiment where a semi-conductor is chosen for the environmental reactive layer 804, the device 800 acts as a light-enhanced chemical detection device, or monitor (e.g. dose-meter) for radiation. In this embodiment, the intensity of UV radiation incident on the device 800 can be correlated to the chemical change of the environmental reactive layer 804 (e.g. oxidation of silicon in presence of oxygen and water, common atmospheric conditions, under the influence of UV). This correlation is achieved by monitoring, as in step 1508 of FIG. 15, the optical properties of the device 800 which are affected as the light-accelerated chemical change results in a change in the optical absorption of the environmental reactive layer 804. In another embodiment, the device 800 is exposed to a particular dose of light to adjust the rate at which the environmental reactive layer reacts to the pre-determined environmental condition.

While the above detailed description has shown, described and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. An environmental condition monitoring device comprising:
   an interferometric modulator comprising:
      a substrate;
      an optical enhancement layer disposed on the substrate, the optical enhancement layer comprising a reflector layer,
      an environmental reactive layer disposed on the optical enhancement layer, the environmental reactive layer having a composition, the composition of the environmental reactive layer configured to alter in response to exposure to an environmental condition;
      the environmental reactive layer and reflector layer defining boundaries for an interferometric cavity of the interferometric modulator, the environmental reactive layer being configured to act as an absorber layer of the interferometric modulator, a thickness of the environmental reactive layer being less than a thickness of the reflector layer, a reflectivity spectrum of the interferometric modulator being a function of the composition of the environmental reactive layer, wherein the environmental reactive layer is one of the following: a metal, a metal alloy, and a semiconductor.

2. The environmental condition monitoring device of claim 1, wherein a thickness of the environmental reactive layer is less than 10 nm.

3. The environmental condition monitoring device of claim 1, wherein the environmental condition is water.

4. The environmental condition monitoring device of claim 1, wherein the environmental condition is a gas species.

5. The environmental condition monitoring device of claim 1, wherein a rate at which the composition of the environmental reactive layer alters in response to exposure to an environmental condition is altered by the dose of light to which the environmental reactive layer is exposed.

6. The environmental condition monitoring device of claim 1, wherein a rate at which the composition of the environmental reactive layer alters in response to exposure to an environmental condition is altered by the temperature to which the environmental reactive layer is exposed.

7. The environmental condition monitoring device of claim 1, further comprising a dielectric layer.

8. The environmental condition monitoring device of claim 1, wherein the environmental reactive layer is a metal.

9. The environmental condition monitoring device of claim 1, wherein the environmental reactive layer is a semi-conductor.

10. The environmental condition monitoring device of claim 1, wherein the reflectivity of the interferometric modulator at a selected wavelength is a function of the composition of the environmental reactive layer.

11. The environmental condition monitoring device of claim 1, wherein a chromaticity of the interferometric modulator is a function of the composition of the environmental reactive layer.

12. An environmental condition monitoring device comprising:
   a substrate;
   an optical enhancement means disposed on the substrate, the optical enhancement means comprising a light reflecting means; and
   an absorber for altering the reflectivity spectrum of the light reflecting means in response to exposure to an environmental condition, wherein the absorber is disposed on the optical enhancement means,
   the absorber and reflecting means defining boundaries for an interferometric cavity, a thickness of the absorber being less than a thickness of the reflecting means, wherein the absorber is one of the following: a metal, a metal alloy, and a semiconductor.

13. The environmental condition monitoring device of claim 12, further comprising an interferometric modulator.

14. The environmental condition monitoring device of claim 12, wherein the absorber comprises an environmental reactive layer having a composition, the composition configured to alter in response to exposure to an environmental condition.

15. A method of manufacturing an environmental condition monitoring device, the method comprising:
   providing a substrate;
   forming an optical enhancement layer on the substrate, the optical enhancement layer including a reflector layer,
   forming an environmental reactive layer on the optical enhancement layer,
   the environmental reactive layer and reflector layer defining boundaries for an interferometric cavity of an interferometric modulator, the environmental reactive layer being configured to act as an absorber layer of the interferometric modulator, a thickness of the environmental reactive layer being less than a thickness of the reflector layer, a reflectivity of the interferometric modulator being a function of the composition of the environmental reactive layer, wherein the environmental reactive layer is one of the following: a metal, a metal alloy, and a semiconductor.

16. The method of claim 15, further comprising configuring the interferometric modulator or the environmental reactive layer, so the reflectivity of the interferometric modulator at a selected wavelength is a function of the composition of the environmental reactive layer.

17. The method of claim 15, further comprising configuring the interferometric modulator to track changes in chromaticity of the interferometric modulator and the appearance of pinholes in the environmental reactive layer in response to exposure to the environmental condition.

18. A method of detecting exposure to an environmental condition, the method comprising:
   providing an interferometric modulator having a reflector layer configured to substantially reflect light disposed on a substrate, and an environmental reactive layer, the environmental reactive layer disposed on a dielectric layer disposed on the reflector layer, a composition of the environmental reactive layer being configured to alter in response to exposure to the environmental condition, the environmental reactive layer and reflector layer defining boundaries for an interferometric cavity of the interferometric modulator, the environmental reactive layer being configured to act as an absorber layer of the interferometric modulator, a thickness of the environmental reactive layer being less than a thickness of the reflector layer, a reflectivity of the interferometric modulator being a function of the composition of the environmental reactive layer, wherein the environmental reactive layer is one of the following: a metal, a metal alloy, and a semiconductor.

19. The method of claim 18, further comprising monitoring a change in chromaticity of the interferometric modulator and the appearance of pinholes in the environmental reactive layer in response to exposure to the environmental condition.

* * * * *